(12) United States Patent
Bilenko et al.

(10) Patent No.: US 9,625,372 B2
(45) Date of Patent: Apr. 18, 2017

(54) ULTRAVIOLET-BASED OZONE SENSOR

(71) Applicant: Sensor Electronic Technology, Inc., Columbia, SC (US)

(72) Inventors: Yuri Bilenko, Columbia, SC (US); Alexander Dobrinsky, Providence, RI (US); Michael Shur, Latham, NY (US); Remigijus Gaska, Columbia, SC (US)

(73) Assignee: Sensor Electronic Technology, Inc., Columbia, SC (US)

( * ) Notice: Subject to any disclaimer, the term of this patent is extended or adjusted under 35 U.S.C. 154(b) by 682 days.

(21) Appl. No.: 13/863,437

(22) Filed: Apr. 16, 2013

(65) Prior Publication Data

US 2013/0270429 A1 Oct. 17, 2013

Related U.S. Application Data

(60) Provisional application No. 61/624,716, filed on Apr. 16, 2012.

(51) Int. Cl.
*G01D 18/00* (2006.01)
*G01N 21/33* (2006.01)
*G01N 21/03* (2006.01)
*G01N 21/05* (2006.01)

(52) U.S. Cl.
CPC ........... *G01N 21/33* (2013.01); *G01N 21/031* (2013.01); *G01N 21/05* (2013.01)

(58) Field of Classification Search
CPC . H04N 5/33; G01J 5/522; A61B 6/583; G01T 1/40; G01D 18/00
See application file for complete search history.

(56) References Cited

U.S. PATENT DOCUMENTS

| | | | |
|---|---|---|---|
| 5,644,070 A | 7/1997 | Gibboney et al. | |
| 5,701,009 A * | 12/1997 | Griffiths et al. | 250/356.1 |
| 5,703,374 A * | 12/1997 | Caprari | 250/492.2 |
| 6,410,940 B1 * | 6/2002 | Jiang et al. | 257/82 |
| 6,911,179 B2 | 6/2005 | Ando et al. | |
| 7,069,769 B2 | 7/2006 | Kung | |
| 7,372,573 B2 * | 5/2008 | Spartz et al. | 356/451 |
| 8,980,178 B2 * | 3/2015 | Gaska et al. | 422/62 |

(Continued)

FOREIGN PATENT DOCUMENTS

CN 102564949 B * 3/2014

OTHER PUBLICATIONS

Tanslation of CN 102564949 B.*

(Continued)

*Primary Examiner* — David Porta
*Assistant Examiner* — Mamadou Faye
(74) *Attorney, Agent, or Firm* — LaBatt, LLC (57) ABSTRACT

A solution for evaluating a sample gas for a presence of a trace gas, such as ozone, is provided. The solution uses an ultraviolet source and an ultraviolet detector mounted in a chamber. The chamber can include reflecting walls and/or structures configured to guide ultraviolet light. A computer system can operate the ultraviolet source in a high power pulse mode and acquire data corresponding to an intensity of the ultraviolet radiation detected by the ultraviolet detector while a sample gas is present in the chamber. Using the data, the computer system can determine a presence and/or an amount of the trace gas in the sample gas.

20 Claims, 9 Drawing Sheets

(56) References Cited

U.S. PATENT DOCUMENTS

| | | | |
|---|---|---|---|
| 2006/0104858 A1* | 5/2006 | Potember | A61L 9/015 422/4 |
| 2007/0114421 A1* | 5/2007 | Maehlich | G01N 21/0303 250/343 |
| 2008/0102204 A1* | 5/2008 | Elers | 427/249.1 |
| 2008/0212216 A1* | 9/2008 | Milosevic et al. | 359/850 |
| 2008/0259341 A1* | 10/2008 | Short | G01N 21/8483 356/437 |
| 2010/0034669 A1* | 2/2010 | Imholt | 417/51 |
| 2010/0078574 A1* | 4/2010 | Cooper et al. | 250/455.11 |
| 2010/0157252 A1* | 6/2010 | Itoh | 353/31 |
| 2010/0200740 A1* | 8/2010 | Ino et al. | 250/251 |
| 2010/0255525 A1 | 10/2010 | Koide et al. | |
| 2010/0296971 A1 | 11/2010 | Gaska et al. | |
| 2011/0299076 A1* | 12/2011 | Feitisch | G01J 3/28 356/326 |
| 2012/0006098 A1 | 1/2012 | Degner et al. | |

OTHER PUBLICATIONS

Ridley et al., "A Small High-Sensitivity, Medium-Response Ozone Detector Suitable for Measurements from Light Aircraft", Journal of Atmospheric and Oceanic Technology, Apr. 1992, pp. 142-148, vol. 9, No. 2.

Faglia et al., "Electrical and structural properties of RGTO-In2O3 sensors for ozone detection", Sensors and Actuators B: Chemical,Sep. 1999, pp. 188-191, vol. 57, No. 1-3.

Shahnazi, "Frequency Modulation Spectroscopy with a Tunable CO_2 Sideband Laser: Ozone Detection", Applied Optics, Apr. 1998, pp. 2502-2504, vol. 37, No. 12.

Gondal et al., "Highly sensitive electronically modulated photoacoustic spectrometer for ozone detection", 2007, pp. 7083-7090, vol. 46, No. 29.

Kiriakidis et al., "Highly Sensitive InOx Ozone Sensing Films on Flexible Substrates", Journal of Sensors, 2009, pp. 1-5, vol. 2009.

Ando, "Optical ozone detection by use of polyaniline film", Solid State Ionics, Dec. 2002, pp. 819-822, vol. 152-153.

Silva et al, "Photoacoustic detection of ozone using a quantum cascade laser", Applied Physics B: Lasers and Optics, Apr. 2004, pp. 677-680, vol. 78, No. 6.

Wang et al., "Real-Time Ozone Detection Based on a Microfabricated Quartz Crystal Tuning Fork Sensor" Sensors, Jul. 2009, pp. 5655-5663, vol. 9, No. 7.

Chien et al., "Standoff detection of ozone in an open environment using photoacoustic spectroscopy technique", Applied Physics Letters, 2012, pp. 104102, vol. 100, No. 10.

Parameswaran et al., "Compact ozone photometer based on UV LEDs", IEEE Photonics Society, 2010 23rd Annual Meeting, 2010, pp. 375-376.

Degner et al., "LED based spectroscopy—A low cost solution for high resolution concentration measurements e.g. for gas monitoring applications", Sensing Technology (ICST), 2011 Fifth International Conference, 2011, pp. 145-150.

* cited by examiner

ULTRAVIOLET-BASED OZONE SENSOR

REFERENCE TO RELATED APPLICATIONS

The current application claims the benefit of U.S. Provisional Application No. 61/624,716, titled "Ozone Sensor Based on Ultraviolet Light Emitting Diode and Photodiode," which was filed on 16 Apr. 2012, and which is hereby incorporated by reference.

TECHNICAL FIELD

The disclosure relates generally to ozone detection, and more particularly, to ultraviolet light emitting diode (UV LED)-based ozone detection.

BACKGROUND ART

Excess levels of ozone can be dangerous to the health of humans. As a result, there are strict regulations regarding human exposure to large doses of ozone. To warn the public of a high concentration of ozone in the atmosphere, ozone levels are monitored using ozone detectors. Current ozone detectors generally fall into three classes: detectors that operate based on ozone light absorption; detectors that operate based on semiconductor devices designed to sense ozone in air passed over the semiconductor device; and detectors that utilize electrochemical effects.

The detectors that operate based on ozone light absorption take advantage of the Beer-Lambert absorption law of ultraviolet (UV) light passing through ambient gas in a chamber that contains ozone. Since ozone strongly absorbs UV radiation, a concentration of ozone can be inferred from a measured amount of UV absorption. The Beer-Lambert law can be applied to calculate the ozone concentration based on the UV absorption detected using an optical source-detector couple. Typically, these devices utilize mercury discharge lamps, which necessitate relatively large detectors with lamps having a limited operational lifetime. Additionally, these devices typically require a chamber having a size in the tens of centimeters in order to successfully detect small levels of ozone.

The detectors that operate based on semiconductor devices designed to sense ozone in air passed over the semiconductor device have a high sensitivity not only to ozone, but other gases and trace elements present in the atmosphere, such as, for example, traces of organic compounds. Calibration of these detectors may be less effective as the devices age and/or interact with different environmental factors affecting an overall performance of the detector. The detectors that utilize electrochemical effects often cannot accurately register small levels of ozone concentration present in the atmosphere, which, nevertheless, can be hazardous to human health.

SUMMARY OF THE INVENTION

Aspects of the invention provide a solution for evaluating a sample gas for a presence of a trace gas, such as ozone. The solution uses an ultraviolet source and an ultraviolet detector mounted in a chamber. The chamber can include reflecting walls and/or structures configured to guide ultraviolet light. A computer system can operate the ultraviolet source in a high power pulse mode and acquire data corresponding to an intensity of the ultraviolet radiation detected by the ultraviolet detector while a sample gas is present in the chamber. Using the data, the computer system can determine a presence and/or an amount of the trace gas in the sample gas.

A first aspect of the invention provides a system comprising: a chamber; an ultraviolet source mounted on a first interior side of the chamber; an ultraviolet detector mounted on the first interior side of the chamber, wherein the chamber is defined by a plurality of reflecting walls having an ultraviolet reflection coefficient of at least eighty percent; and a computer system for evaluating a sample gas in the chamber for a presence of a trace gas by performing a method including: operating the ultraviolet source in a high power pulse mode; acquiring data corresponding to an intensity of ultraviolet radiation detected by the ultraviolet detector during the operating; and determining the presence of the trace gas using the acquired data.

A second aspect of the invention provides a system comprising: a chamber having an inlet and an outlet; a pumping system for introducing a gas into the chamber through the inlet; an ultraviolet source mounted on a first interior side of the chamber; an ultraviolet detector mounted on the first interior side of the chamber; and a computer system for evaluating a sample gas in the chamber for a presence of ozone by performing a method including: operating the pumping system to introduce the sample gas into the chamber, wherein the operating includes operating the pumping system with both the inlet and the outlet open for a sufficient time to allow at least three chamber volumes of gas to leave the chamber through the outlet; sealing the chamber; operating the ultraviolet source in a high power pulse mode after the sealing; acquiring data corresponding to an intensity of ultraviolet radiation detected by the ultraviolet detector during the operating; and determining the presence of ozone in the sample gas using the acquired data.

A third aspect of the invention provides a method of evaluating a sample gas in a chamber for a presence of ozone, the method comprising: a computer system operating a pumping system with a filter removing ozone from gas entering the chamber; the computer system operating the pumping system without the filter removing ozone to introduce the sample gas into the chamber, wherein the operating includes operating the pumping system with both an inlet and an outlet of the chamber open for a sufficient time to allow at least three chamber volumes of gas to leave the chamber through the outlet; the computer system sealing the chamber; the computer system operating the ultraviolet source in a high power pulse mode after the sealing; the computer system acquiring data corresponding to an intensity of ultraviolet radiation detected by the ultraviolet detector during the operating; and the computer system determining the presence of ozone in the sample gas using the acquired data.

Other aspects of the invention provide methods, systems, program products, and methods of using and generating each, which include and/or implement some or all of the actions described herein. The illustrative aspects of the invention are designed to solve one or more of the problems herein described and/or one or more other problems not discussed.

BRIEF DESCRIPTION OF THE DRAWINGS

These and other features of the disclosure will be more readily understood from the following detailed description of the various aspects of the invention taken in conjunction with the accompanying drawings that depict various aspects of the invention.

It is noted that the drawings may not be to scale. The drawings are intended to depict only typical aspects of the invention, and therefore should not be considered as limiting the scope of the invention. In the drawings, like numbering represents like elements between the drawings.

DETAILED DESCRIPTION OF THE INVENTION

As indicated above, aspects of the invention provide a solution for evaluating a sample gas for a presence of a trace gas, such as ozone. The solution uses an ultraviolet source and an ultraviolet detector mounted in a chamber. The chamber can include reflecting walls and/or structures configured to guide ultraviolet light. A computer system can operate the ultraviolet source in a high power pulse mode and acquire data corresponding to an intensity of the ultraviolet radiation detected by the ultraviolet detector while a sample gas is present in the chamber. Using the data, the computer system can determine a presence and/or an amount of the trace gas in the sample gas. The solution can provide a compact detector, which can overcome one or more shortcomings associated with previous mercury lamp-based solutions. As used herein, unless otherwise noted, the term "set" means one or more (i.e., at least one) and the phrase "any solution" means any now known or later developed solution.

Figure 1:
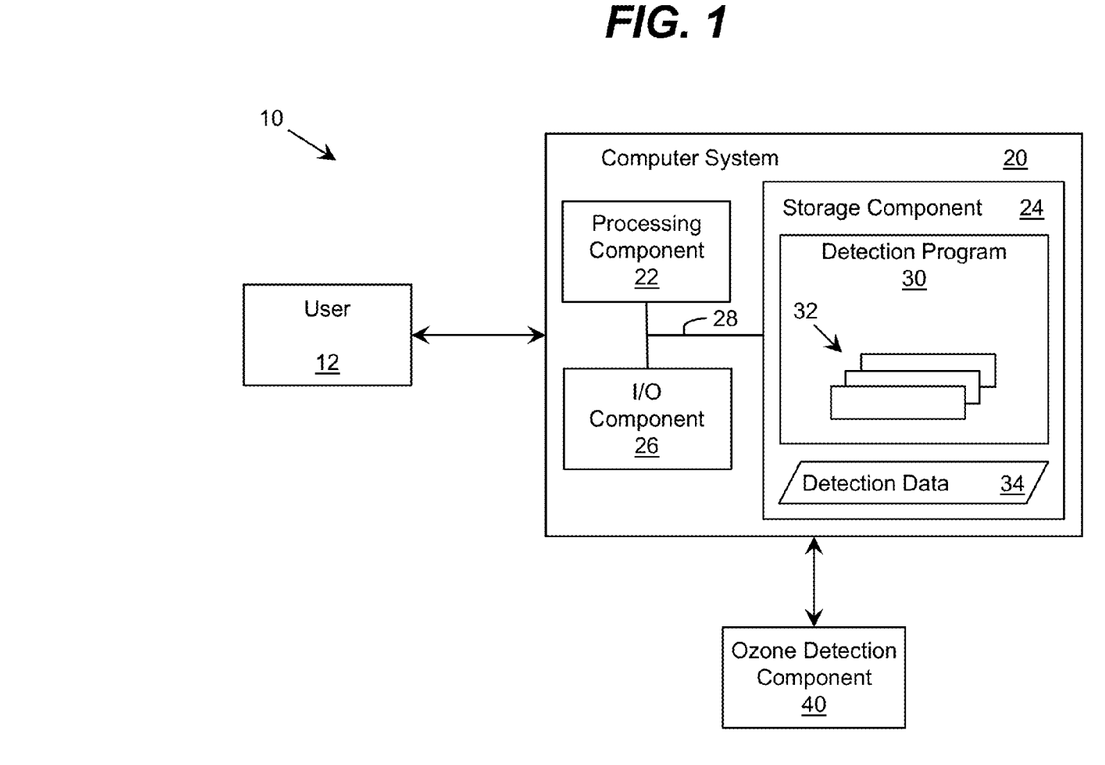
FIG. 1 shows an illustrative environment for detecting a trace gas in an atmosphere according to an embodiment.

Turning to the drawings, FIG. 1 shows an illustrative environment 10 for detecting a trace gas, such as ozone, in an atmosphere according to an embodiment. To this extent, the environment 10 includes a computer system 20 that can perform a process described herein in order to detect a presence and/or amount of a targeted trace gas in the atmosphere. In particular, the computer system 20 is shown including a detection program 30, which makes the computer system 20 operable to detect and/or measure an amount of the targeted trace gas by performing a process described herein.

The computer system 20 is shown including a processing component 22 (e.g., one or more processors), a storage component 24 (e.g., a storage hierarchy), an input/output (I/O) component 26 (e.g., one or more I/O interfaces and/or devices), and a communications pathway 28. In general, the processing component 22 executes program code, such as the detection program 30, which is at least partially fixed in storage component 24. While executing program code, the processing component 22 can process data, which can result in reading and/or writing transformed data from/to the storage component 24 and/or the I/O component 26 for further processing. The pathway 28 provides a communications link between each of the components in the computer system 20. The I/O component 26 can comprise one or more human I/O devices, which enable a human user 12 to interact with the computer system 20 and/or one or more communications devices to enable a system user 12 to communicate with the computer system 20 using any type of communications link. To this extent, the detection program 30 can manage a set of interfaces (e.g., graphical user interface(s), application program interface, and/or the like) that enable human and/or system users 12 to interact with the detection program 30. Furthermore, the detection program 30 can manage (e.g., store, retrieve, create, manipulate, organize, present, etc.) the data, such as detection data 40, using any solution.

In any event, the computer system 20 can comprise one or more general purpose computing articles of manufacture (e.g., computing devices) capable of executing program code, such as the detection program 30, installed thereon. As used herein, it is understood that "program code" means any collection of instructions, in any language, code or notation, that cause a computing device having an information processing capability to perform a particular action either directly or after any combination of the following: (a) conversion to another language, code or notation; (b) reproduction in a different material form; and/or (c) decompression. To this extent, the detection program 30 can be embodied as any combination of system software and/or application software.

Furthermore, the detection program 30 can be implemented using a set of modules 32. In this case, a module 32 can enable the computer system 20 to perform a set of tasks used by the detection program 30, and can be separately developed and/or implemented apart from other portions of the detection program 30. As used herein, the term "component" means any configuration of hardware, with or without software, which implements the functionality described in conjunction therewith using any solution, while the term "module" means program code that enables a computer system 20 to implement the actions described in conjunction therewith using any solution. When fixed in a storage component 24 of a computer system 20 that includes a processing component 22, a module is a substantial portion of a component that implements the actions. Regardless, it is understood that two or more components, modules, and/or systems may share some/all of their respective hardware and/or software. Furthermore, it is understood that some of the functionality discussed herein may not be implemented or additional functionality may be included as part of the computer system 20.

When the computer system 20 comprises multiple computing devices, each computing device can have only a portion of the detection program 30 fixed thereon (e.g., one or more modules 32). However, it is understood that the computer system 20 and the detection program 30 are only representative of various possible equivalent computer systems that may perform a process described herein. To this extent, in other embodiments, the functionality provided by the computer system 20 and the detection program 30 can be at least partially implemented by one or more computing devices that include any combination of general and/or specific purpose hardware with or without program code. In each embodiment, the hardware and program code, if included, can be created using standard engineering and programming techniques, respectively.

Regardless, when the computer system 20 includes multiple computing devices, the computing devices can communicate over any type of communications link. Furthermore, while performing a process described herein, the computer system 20 can communicate with one or more other computer systems using any type of communications link. In either case, the communications link can comprise any combination of various types of optical fiber, wired, and/or wireless links; comprise any combination of one or more types of networks; and/or utilize any combination of various types of transmission techniques and protocols.

As discussed herein, the detection program 30 enables the computer system 20 to detect a presence of and/or measure an amount of a targeted trace gas in an atmosphere. Additional aspects of the invention are shown and described in conjunction with the detection and/or measurement of an amount of ozone in an atmosphere, such as the earth's atmosphere, an atmosphere in a workplace environment, an atmosphere in an enclosed environment (e.g., a submarine), and/or the like. However, it is understood that various other trace gases can be targeted in any atmosphere using the teachings described herein.

The computer system 20 can operate various devices included in the ozone detection component 40 in order to detect and/or measure an amount of ozone in the atmosphere. During operation of the various devices in the ozone detection component 40, the computer system 20 can receive and process detection data 34 to evaluate the atmosphere for the presence of ozone. The computer system 20 can store data corresponding to the evaluation (e.g., a result, a timestamp, and/or the like) as detection data 34. Furthermore, the computer system 20 can provide some or all of the detection data 34 for use by the user 12. The detection data 34 can include, for example, a level of the ozone detected, an alarm condition generated in response to a level of ozone detected, and/or the like. In response to receiving the detection data 34, the user 12 can take any of various actions.

Figure 2A:
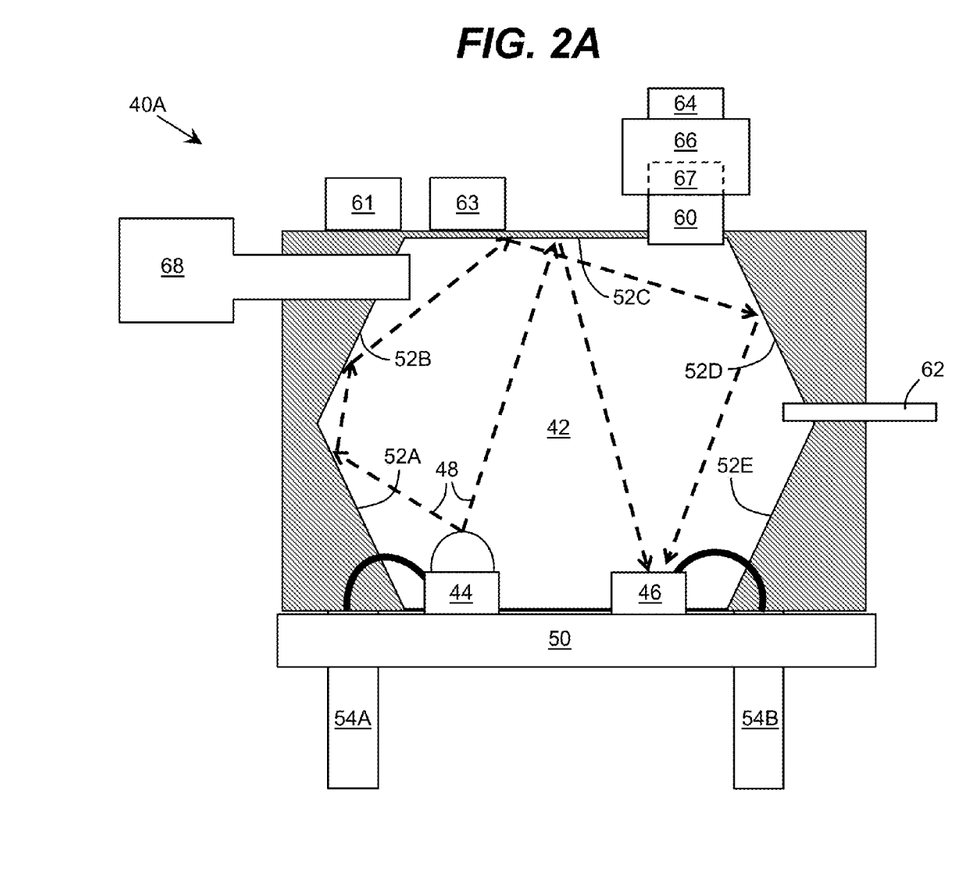
FIGS. 2A-2C show illustrative ozone detection components according to embodiments.
Figure 2B:
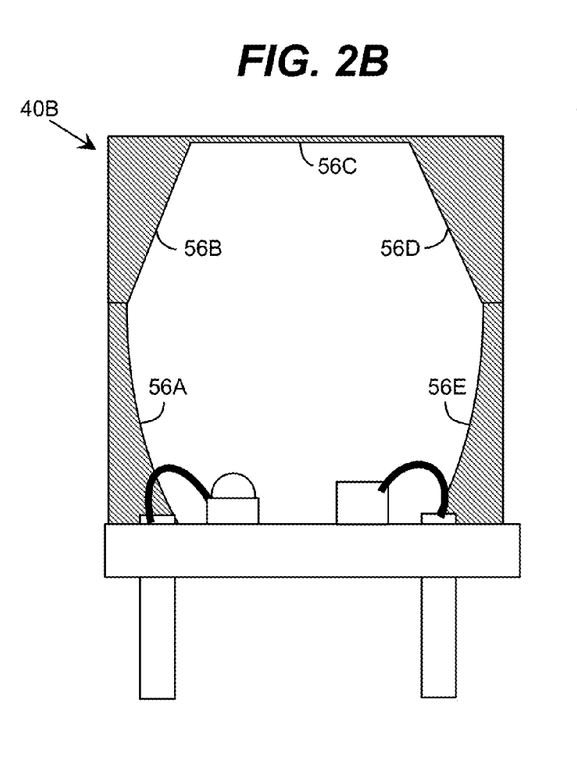
Figure 2C:
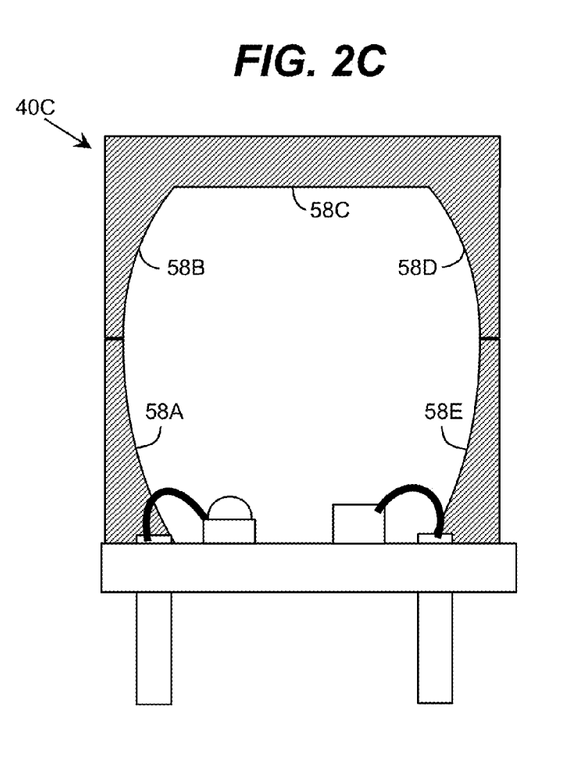

FIGS. 2A-2C show illustrative ozone detection components 40A-40C according to embodiments. As shown in FIG. 2A, an ozone detection component 40A can include a chamber 42, an ultraviolet source 44, and an ultraviolet detector 46. The ultraviolet source 44 and the ultraviolet detector 46 can be located in a close proximity to each other. As illustrated, the ultraviolet source 44 can be configured to emit ultraviolet light 48 into the chamber 42, and the ultraviolet detector 46 can be configured to detect the ultraviolet light 48 after it travels through the chamber 42. When acquiring measurement data, the ultraviolet source 44 can be operated in a pulsed mode delivering maximum ultraviolet power into the chamber 42. For example, the pulsed mode can have a frequency up to approximately one gigahertz, and can assist in filtering noise in the data acquired by the ultraviolet source 44. The chamber 42 can have any size. For example, the chamber 42 can have dimensions between approximately ten and approximately thirty cubic centimeters.

In an embodiment, the ultraviolet source 44 is an ultraviolet light emitting diode (LED). In a more particular embodiment, the ultraviolet LED is a deep ultraviolet LED configured to emit ultraviolet light 48 having a peak wavelength between approximately 240 and approximately 290 nanometers. The ultraviolet source 44 can be a group III-nitride based semiconductor. Illustrative group III-nitride based LEDs include layers formed from alloys of any of various combinations of one or more of: boron (B); indium (In); aluminum (Al); and gallium (Ga), and nitrogen (N). Such a layer can be of the form $Ga_zIn_yAl_xB_{1-x-y-z}N$, where x, y, and z indicate the molar fraction of a given element, where $0 \leq x, y, z \leq 1$, and where $0 \leq x+y+z \leq 1$.

In an embodiment, the ultraviolet source 44 is configured to emit ultraviolet light 48 having a prescribed angular distribution such that ultraviolet rays emitted at different angles travel, in general, different optical paths prior to being detected by the ultraviolet detector 46. For example, the ultraviolet source 44 can include a device structure formed (e.g., epitaxially grown) on a substrate through which the ultraviolet light will be emitted from the ultraviolet source 44. The substrate can comprise any suitable substrate including, for example, sapphire, AlN, GaN, AlGaN, zinc oxide (ZnO), lithium gallate ($LiGaO_2$), lithium aluminate ($LiAlO_2$), and/or the like. The exterior sides of the substrate can be shaped (e.g., tapered) to control the angular distribution of ultraviolet light 48 from the ultraviolet source 44 using any solution (e.g., an etching process, scribed with a laser, and/or the like).

It is understood that while the ultraviolet source 44 is shown located within the chamber 42, other solutions can be implemented for emitting ultraviolet light 48 within the chamber 42. For example, an ultraviolet source 44 can be located external to the chamber 42, and ultraviolet light 48 can be directed from the ultraviolet source 44 into the chamber 42 using wave guiding means (e.g., optical fiber(s)). In this case, multiple optical fibers can extend into the chamber 42 and be configured to emit ultraviolet light 48 having the prescribed angular distribution. Similarly, it is understood that two or more ultraviolet sources 44 can be used to generate ultraviolet light 48 within the chamber 42.

The ultraviolet detector 46 can comprise any type of device whose operation is altered in response to one or more properties of incident ultraviolet light having a wavelength within a target range of wavelengths. For example, one or more attributes of a signal generated by the ultraviolet detector 46 can be altered based on a presence of the ultraviolet radiation, an amount of the ultraviolet radiation, and/or the like, which is incident to a detecting surface of the ultraviolet detector 46. Furthermore, the ultraviolet detector 46 can have sufficient sensitivity to enable measurement data having a desired accuracy. For example, the ultraviolet detector 46 can have a sensitivity of approximately one microwatt per square centimeter. In an embodiment, the ultraviolet detector 46 is a photodetector. In another embodiment, the ultraviolet detector 46 comprises an ultraviolet LED operated in reverse bias. In a further embodiment, both the ultraviolet source 44 and the ultraviolet detector 46 are devices capable of being operated as an emitting device (e.g., when operated under forward bias) or a detecting device (e.g., when operated under reverse bias). In this case, the computer system 20 (FIG. 1) can change operation of the devices using any solution (e.g., alternating source/detector, changing the operation after a period of operation, and/or the like). While a single ultraviolet detector 46 is shown, it is understood that the ozone detection component 40A can include any number of one or more ultraviolet detectors 46.

The chamber 42 is shown formed by a chamber floor 50 and a plurality of chamber walls 52A-52E. In an embodiment, the chamber floor 50 comprises a material having a low thermal expansion. For example, the material can comprise a metal, such as that used in the transistor outline (TO) package, TO-39, or a similar package. The chamber floor 50 can include sets of pins 54A, 54B for use in connecting each of the ultraviolet devices 44, 46, respectively, to a circuit (e.g., the computer system 20 shown in FIG. 1). The chamber walls 52A-52E can be formed of any suitable material. The material can be reflective of ultraviolet radiation having the target wavelength and/or can be coated with a material reflective of ultraviolet radiation. In either case, the chamber walls 52A-52E can have an ultraviolet reflection coefficient of at least eighty percent. For example, the chamber walls 52A-52E can be formed of or covered by highly ultraviolet-reflective aluminum.

Each of the chamber walls 52A-52E is shown having a substantially flat interior surface. In an embodiment, the chamber 42 is defined by one or more chamber walls having a parabolic interior surface. For example, FIG. 2B shows an illustrative ozone detection component 40B in which the chamber walls 56A, 56E have a parabolic shape, while the chamber walls 56B-56D are substantially flat surfaces. Similarly, FIG. 2C shows an illustrative ozone detection component 40C in which the chamber walls 58A, 58B, 58D, 58E have interior surfaces of parabolic shapes while the chamber wall 58C has a substantially flat interior surfaces. In either case, the parabolic shapes can be configured to increase a number of reflections of the ultraviolet radiation prior to being detected by the ultraviolet detector.

Returning to FIG. 2A, the ozone detection component 40A further includes an inlet 60 and an outlet 62. During operation of the ozone detection component 40A, a sample gas (e.g., air from the earth's atmosphere) can be selectively introduced into the chamber through the inlet 60, and gas can be selectively allowed to leave the chamber through the outlet 62. To this extent, the inlet 60 and the outlet 62 can each include a valve, or the like, which is operable (e.g., by the computer system 20), to allow or not allow the flow of a gas through the corresponding opening.

A pumping system 64 can be located adjacent to the inlet 50, and can be operated (e.g., by the computer system 20) to force a gas into the chamber 42. The pumping system 64 can comprise any type of pumping system 64, such as a vacuum pump, a fan, and/or the like, which can be operated to draw the gas into the chamber 42 at a target pressure. It is understood that while the pumping system 64 is shown located adjacent to the inlet 50, a pumping system can be located adjacent to the outlet 62. In this case, such a pumping system can be operated to force gas out of the chamber 42, thereby causing a gas to enter the chamber through the inlet 60.

The ozone detection component 40A also is shown including a filtering unit 66 located adjacent to the inlet 60 (e.g., between the inlet 60 and the pumping system 64). The filtering unit 66 can comprise a combination of one or more of any type of filter capable of filtering large (e.g., few microns size) and/or small (e.g., 0.3 microns) elements that may be present in the atmosphere. Additionally, the filtering unit 66 can include one or more filters capable of filtering ultraviolet absorbing materials and gases other than the target trace gas (e.g., ozone), such as organic and other ultraviolet absorbing trace elements. These filters in the filtering unit 66 can be fixed in place such that the gas entering the chamber 42 always has been filtered of the target elements, materials, and/or gases. The filtering unit 66 can include a cleaning mechanism, a monitor for indicating when a filter requires cleaning/changing, and/or the like, which can be operated by the computer system 20 using any solution.

Additionally, the filtering unit 66 can include one or more filters 67, which are capable of being operated by the computer system 20 to selectively filter the gas entering the chamber 42. In an embodiment, the filtering unit 66 includes a filter 67 corresponding to the target trace gas (e.g., ozone), which can be selectively utilized to remove a substantial portion of any of the target trace gas present in the gas prior to its entering the chamber. For example, the filtering unit 66 can include a filter 67 including a catalyst, which converts ozone into oxygen and by-product elements. The filtering unit 66 can be configured to enable selective use of the filter 67 using any solution. For example, the filtering unit 66 can be configured to move/remove the filter 67 from an air flow path, redirect an air flow path (e.g., using one or more deflectors, or the like) to pass through/not pass through the filter 67, and/or the like.

The ozone detection component 40A also is shown including a target trace gas source 68, which can be operated by the computer system 20. In particular, the target trace gas source 68 can produce the target trace gas (e.g., ozone) at any of a set of known concentrations and deliver the target trace gas into the chamber 42 (e.g., via another inlet). In an embodiment, the target trace gas source 68 comprises an ozone generating device, which can generate ozone using any solution (e.g., a discharge arc) and can be selectively operated by the computer system 20 to generate gas having any of a plurality of known concentrations of ozone. A range of the known concentrations can be selected based on an accuracy of the ozone detection component 40A and a range of expected/critical measurement values for the trace gas. In an embodiment, the trace gas is ozone and the range of known concentrations varies between approximately 0.1 ppm to approximately 2 ppm.

Figure 3:
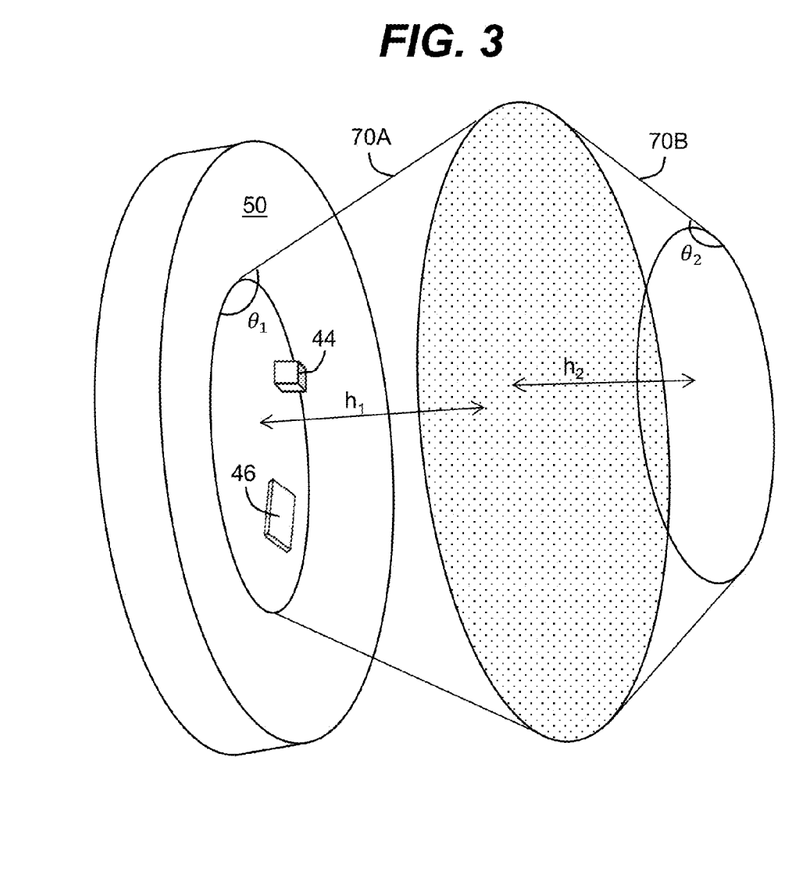
FIG. 3 shows another illustrative configuration of a chamber according to an embodiment.

It is understood that the chamber 42 and the chamber walls 52A-52E are only illustrative of various possible configurations of a chamber for the ozone detection component 40A. To this extent, FIG. 3 shows another illustrative chamber configuration according to an embodiment. In this case, an interior of the chamber is formed by a chamber floor 50, a first conical frustum (truncated cone) 70A attached thereto, and a second conical frustum 70B attached to the first conical frustum 70A. Each conical frustum 70A, 70B has an interior surface that is reflective of ultraviolet radiation. The conical frustums 70A, 70B are configured such that they are attached at their respective bases, which are substantially the same size. A top of the first conical frustum is attached to the chamber floor 50, and a top of the second conical frustum forms a top surface of the interior of the chamber.

Each conical frustum 70A, 70B is characterized by a corresponding opening angle $\Theta_1$, $\Theta_2$, respectively, and a corresponding height $h_1$, $h_2$, respectively. In an embodiment, a shape of the interior of the chamber is configured to result in a target effective optical path that ultraviolet light emitted by the ultraviolet source 44 travels before impinging the ultraviolet detector 46. For example, the target optical path can be selected to be at least a minimum length. To this extent, the opening angles $\Theta_1$, $\Theta_2$ and/or heights $h_1$, $h_2$ can be configured to provide an effective optical path having a minimum length.

Figure 4:
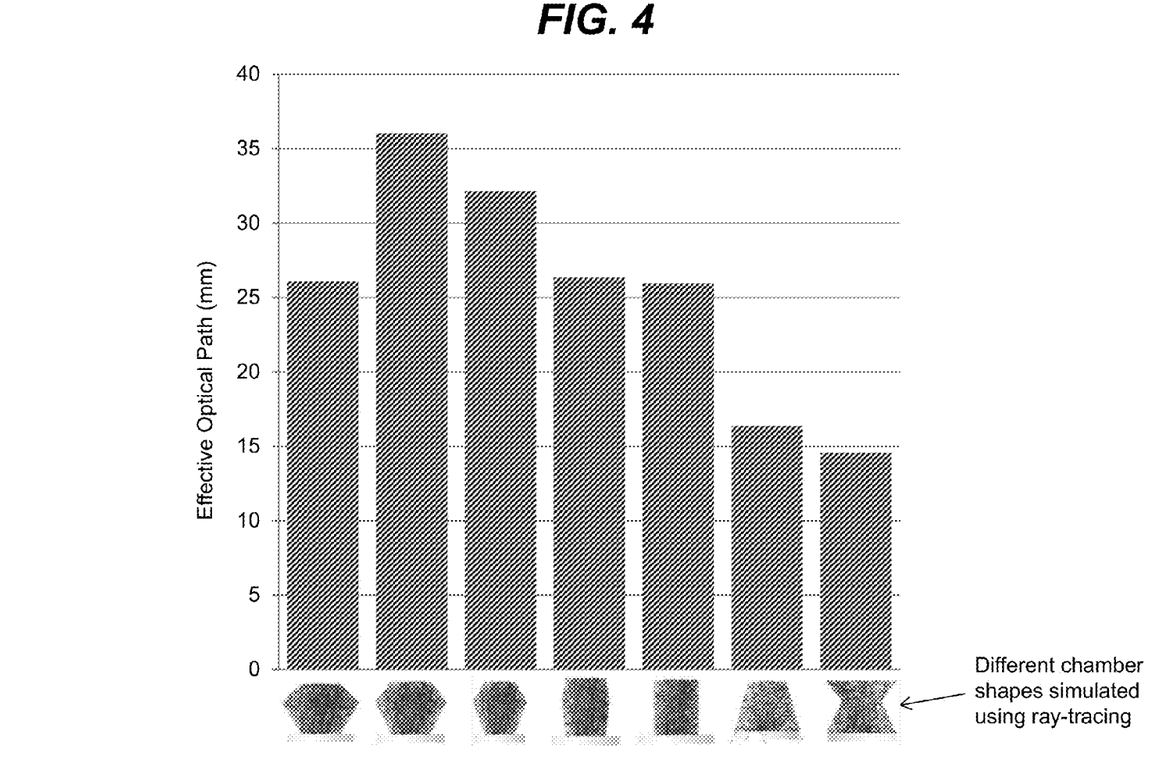
FIG. 4 shows a chart of effective optical paths derived from simulated ray tracing results for various illustrative chamber shape configurations according to an embodiment.

FIG. 4 shows a chart of effective optical paths derived from simulated ray tracing results for various illustrative chamber shape configurations according to an embodiment. A cross section of the chamber shape corresponding to each of the effective optical paths is shown below the corresponding bar. As illustrated, variation in the opening angles $\Theta_1$, $\Theta_2$ affects the length of the effective optical path. In the ray tracing simulations, the longest effective optical path was achieved with opening angles $\Theta_1$, $\Theta_2$ of approximately thirty and forty degrees, respectively. In an embodiment, each of the opening angles $\Theta_1$, $\Theta_2$ is within a range between approximately twenty degrees and approximately fifty degrees. Using the selected angles $\Theta_1$, $\Theta_2$, the corresponding heights $h_1$, $h_2$ can be selected to increase/decrease the value of the effective optical path. Illustrative dimensions used in the simulation are four millimeters for the height $h_1$, 2.4 millimeters for the height $h_2$, bottom radiuses of each conical frustum 70A, 70B of 4.5 millimeters, and top radiuses of each conical frustum 70A, 70B of 2.5 millimeters.

While the embodiments of FIGS. 2A-2C and FIG. 3 describe use of diffuse light, it is understood that collimated ultraviolet light can be used. Use of collimated ultraviolet light also can enable an effective optical path to be increased without requiring a significant increase in the volume of the chamber 42. The collimated ultraviolet light can be generated, for example, by an ultraviolet laser diode. Alternatively, a diffuse ultraviolet LED can generate diffuse ultraviolet light, which is subsequently collimated using, for example, a parabolic reflector.

Figure 5:
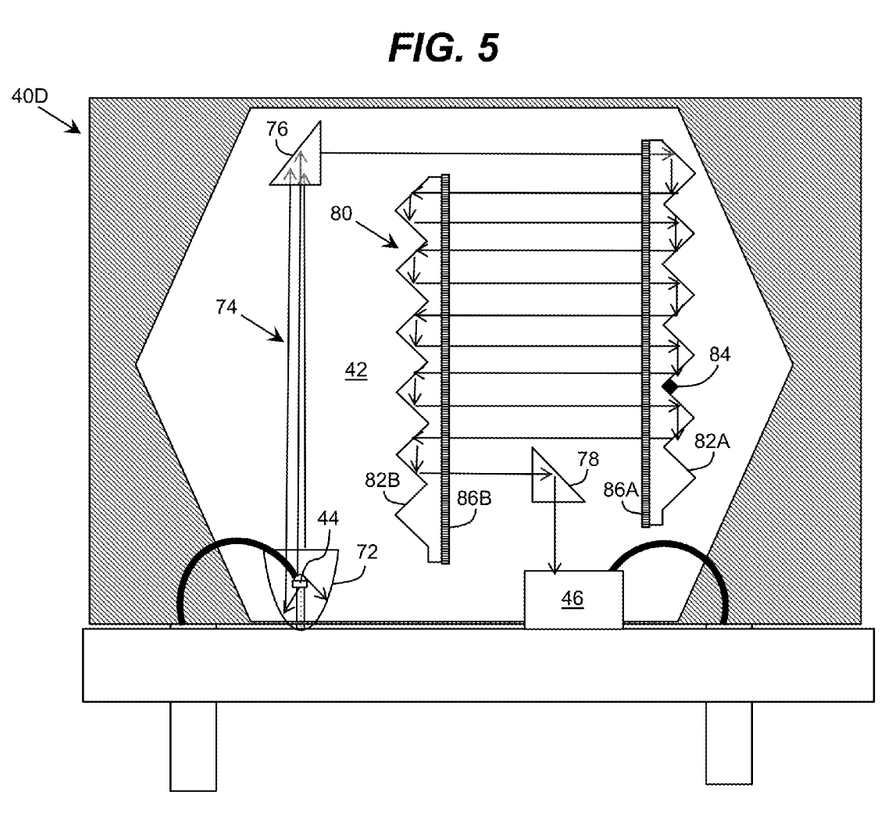
FIG. 5 shows an illustrative ozone detection component according to an embodiment.

To this extent, FIG. 5 shows an illustrative ozone detection component 40D according to an embodiment. While not shown for clarity, it is understood that the ozone detection component 40D can include various components shown in FIG. 2A. In this case, an ultraviolet source 44 is located at a focal point of a parabolic reflector 72. During operation, the ultraviolet source 44 emits diffuse ultraviolet light, which reflects off of the parabolic reflector 72, producing a collimated beam of ultraviolet light 74. A size of the ultraviolet source 44 can be relatively small compared to a diameter of the parabolic reflector 72. In an embodiment, the diameter of the parabolic reflector 72 is at least approximately five times greater than a characteristic size of the ultraviolet source 44. In a further embodiment, the ultraviolet source 44 has sub-millimeter dimensions. The parabolic reflector 72 can be formed of/coated with any material highly reflective of ultraviolet light, such as highly ultraviolet-reflective aluminum.

The chamber 42 also is shown including various beam guiding components. The beam guiding components can be configured to direct the ultraviolet beam 74 onto a surface of the ultraviolet detector 46. Furthermore, the beam guiding components can be configured to cause the ultraviolet beam 74 to travel an effective optical path of a minimum target length. For example, the chamber 42 is shown including a forty-five degree prism 76, which is configured to redirect, e.g., through total internal reflection, the ultraviolet beam 74 onto a grooved plate structure 80. The grooved plate structure 80 includes two grooved plates 82A, 82B, which are positioned in a staggered arrangement. The staggered arrangement of the grooved plates 82A, 82B is configured to cause the ultraviolet beam 74 to reflect back and forth between the grooved plates 82A, 82B before eventually being redirected onto the ultraviolet detector 46 by a prism 78. It is understood that the grooved plate structure 80 is only illustrative of various possible arrangements of optical elements, which can be utilized to increase an optical path traveled by the ultraviolet beam 74.

The grooved plate structure 80 can be fabricated using any solution. In an embodiment, each prism 76, 78 and each of the grooved plates 82A, 82B is fabricated of an ultraviolet transparent material having an index of refraction greater than approximately 1.42 for ultraviolet light having a wavelength corresponding to the peak wavelength emitted by the ultraviolet source 44. Illustrative ultraviolet transparent materials include fused silica, alumina sol-gel glass, alumina aerogel, sapphire, aluminum nitride (e.g., single crystal aluminum nitride), boron nitride (e.g., single crystal boron nitride), and/or the like. The grooved plates 82A, 82B can be fabricated by machining the grooves in the ultraviolet transparent material, with the angle 84 between grooves being ninety degrees. A dimension of each groove (e.g., a length of one of the sides of the prism) can be selected to be substantially larger (e.g., at least two times) than a diameter of the ultraviolet beam 74.

Each grooved plate 82A, 82B also can have an antireflective coating 86A, 86B formed thereon using any solution. For example, the antireflective coating 86A, 86B can comprise an ultraviolet transparent material with a nano-scale roughness on the order of the wavelength of the ultraviolet beam 74. To this extent, a characteristic scale of the variation provided by the nano-scale roughness can be between approximately ten to two hundred percent of the wavelength of the ultraviolet beam 74.

The grooved plate structure 80 can be designed such that any Fresnel reflected ultraviolet light travels the same path as the ultraviolet beam 74, but in the opposite direction. Such Fresnel radiation enters the parabolic reflector 72 and is reflected back towards the ultraviolet detector 46. Regardless, the Fresnel reflectance for normal incident light at an air/prism interface can be relatively small. For example, a prism with refractive index of 1.42 has a Fresnel reflectance of 2.7%.

Figure 6:
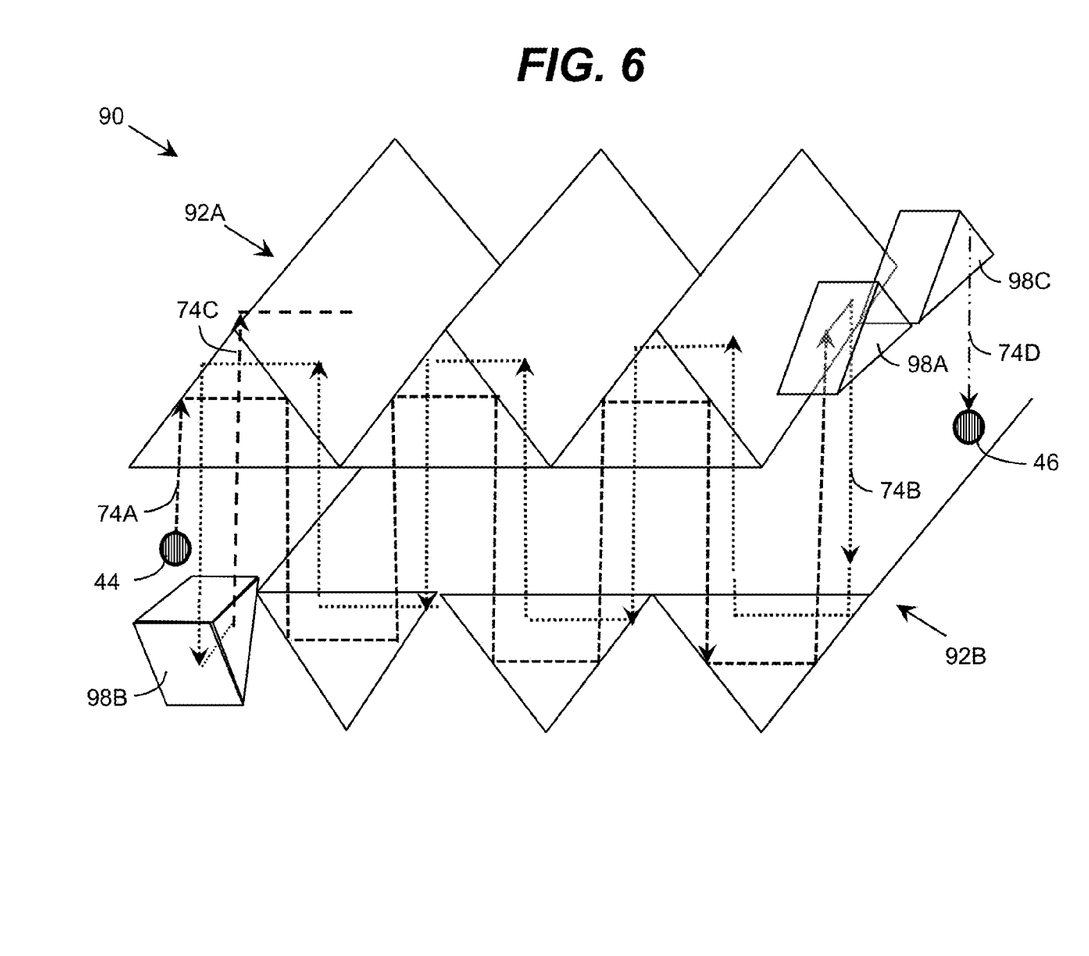
FIG. 6 shows an illustrative beam guiding structure according to an embodiment.

While the grooved plate structure 80 is illustrated as providing two dimensional guiding of the ultraviolet beam 74, it is understood that an embodiment can provide three-dimensional wave guiding, thereby further increasing an optical path of the ultraviolet beam 74. For example, FIG. 6 shows an illustrative beam guiding structure 90 according to an embodiment. The beam guiding structure 90 includes a pair of grooved plates 92A, 92B, which can be fabricated and arranged in the same manner as the grooved plates 82A, 82B (FIG. 5) described herein. To this extent, an ultraviolet source 44 can emit an ultraviolet beam, which travels a first path 74A through the beam guiding structure 90.

The beam guiding structure 90 includes a prism 98A on a first end of a grooved plate 92A, which redirects the ultraviolet beam from the first path 74A to a second path 74B through the beam guiding structure 90. Similarly, the beam guiding structure 90 includes a prism 98B on a second end of a grooved plate 92B, which redirects the ultraviolet beam from the second path 74B to a third path 74C through the beam guiding structure 90. While not shown for clarity, the beam guiding structure 90 can include any number of prisms configured to cause the ultraviolet beam to travel any number of paths through the beam guiding structure 90. An extent to which the optical path can be increased depends on a degree of light collimation, e.g., achieved by the parabolic reflector 72 (FIG. 5), which in turn depends on a size of the ultraviolet source 44 and its characteristic angular distribution of intensity. Regardless, eventually, a prism 98C can redirect the ultraviolet beam out of the beam guiding structure 90 and into a path 74D which terminates at a surface of an ultraviolet detector 46.

Returning to FIGS. 1 and 2A, the computer system 20 can be configured to operate the various devices of the ozone detection component 40A in both a calibration mode and a measurement mode. In an embodiment, the computer system 20 can periodically (e.g., in response to a request from a user 12, based on an amount of operating time, and/or the like) operate the various devices of the ozone detection component 40A in the calibration mode to re-calibrate the ozone detection component 40A. Such re-calibration may be desired to, for example, account for subtle changes in the chamber 42 environment which may be present due to various deposits building up on the chamber walls 52A-52E thereby affecting the measurements acquired using the ultraviolet detector 46.

Figure 7:
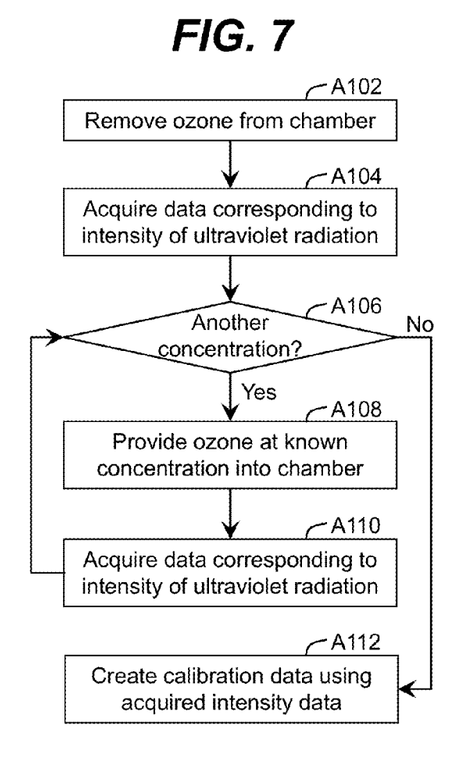
FIG. 7 shows an illustrative process for calibrating an ozone detection component according to an embodiment.

The computer system 20 can calibrate the ozone detection component 40A to empirically determine ultraviolet absorption calibration data for various ozone concentrations, which the computer system 20 can store as detection data 34. To this extent, FIG. 7 shows an illustrative process for calibrating the ozone detection component 40A, which can be implemented by the computer system 20, according to an embodiment.

In action A102, the computer system 20 can remove ozone from the chamber 42 using any solution. For example, the computer system 20 can operate the filtering unit 66 to activate an ozone filter 67 included therein to remove a substantial portion of any ozone present in the gas prior to its entering the chamber 42. While the ozone filter 67 is activated, the computer system 20 can operate the pumping system 64 to cause ozone-filtered gas to enter the chamber 42 through the inlet 60. For an initial startup period, the computer system 20 can open the outlet 62 to allow gas to evacuate the chamber 42 there through. In an embodiment, the initial startup period lasts for an amount of time to allow at least several chamber volumes of gas to evacuate the chamber 42.

In action A104, the computer system 20 can acquire data corresponding to an intensity of the ultraviolet radiation detected by the ultraviolet detector 46. For example, the computer system can turn off the pumping system 64 and seal the chamber 42, e.g., by closing both the outlet 62 and the inlet 60. Additionally, the computer system 20 can operate the ultraviolet source 44 to emit ultraviolet radiation 48, and obtain data corresponding to a detected intensity of the ultraviolet radiation 48 from the ultraviolet detector 46. The computer system 20 can store the data as detection data 34 corresponding to a reference ultraviolet intensity at a zero ozone level.

In action A106, the computer system 20 can determine whether data is to be required for another known ozone concentration as part of the calibration process. If so, in action A108, the computer system 20 can introduce gas having a known concentration of ozone into the chamber 42 using any solution. For example, the computer system 20 can operate the target trace gas source 68, which can be configured to generate a gas with one of a plurality of possible ozone levels and introduce the gas into the chamber 42. For an initial startup period, the computer system 20 can open the outlet 62 to allow gas to evacuate the chamber 42 there through. In an embodiment, the initial startup period lasts for an amount of time to allow at least several chamber volumes of gas to evacuate the chamber 42.

In action A110, the computer system 20 can acquire data corresponding to an intensity of the ultraviolet radiation detected by the ultraviolet detector 46. For example, the computer system can turn off the target trace gas source 68 and seal the chamber 42, e.g., by closing the outlet 62. Additionally, the computer system 20 can operate the ultraviolet source 44 to emit ultraviolet radiation 48, and obtain data corresponding to a detected intensity of the ultraviolet radiation 48 from the ultraviolet detector 46. The computer system 20 can store the data as detection data 34 corresponding to an ultraviolet intensity at the corresponding ozone level.

After acquiring the data for an ozone level, the computer system 20 can determine whether data is to be required for another known ozone concentration as part of the calibration process. If so, the computer system 20 can repeat actions A108 and A110 for the next ozone concentration. In an embodiment, the computer system 20 acquires data for a plurality of non-zero known ozone concentrations as part of the calibration process. Additionally, the computer system 20 can acquire the data by gradually increasing the known ozone concentration in each repetition of actions A108 and A110. Any number of known ozone concentrations can be used over any span of ozone concentrations. In an embodiment, at least the highest known ozone concentration used in the calibration process is higher than an ozone concentration at which an alarm is indicated. For example, the calibration process can use ozone concentrations ranging from 0.1 ppm to 2 ppm, with increments of 0.1 ppm.

In any event, once all of the ozone concentration data has been acquired, in action A112, the computer system 20 can process the acquired concentration data to generate calibration data for the ozone detection component 40A. For example, the computer system 20 can create a reference table, which is stored as detection data 34, including the measured ultraviolet intensity for each of the known ozone concentrations. Furthermore, the computer system 20 can determine an amount of ultraviolet light absorbed at each of the known ozone concentrations, which can be stored in the reference table. Additionally, the computer system 20 can use the acquired measurement data to generate a calibration curve (e.g., using a curve-fitting solution), which the computer system 20 can store as detection data 34.

Figure 8:
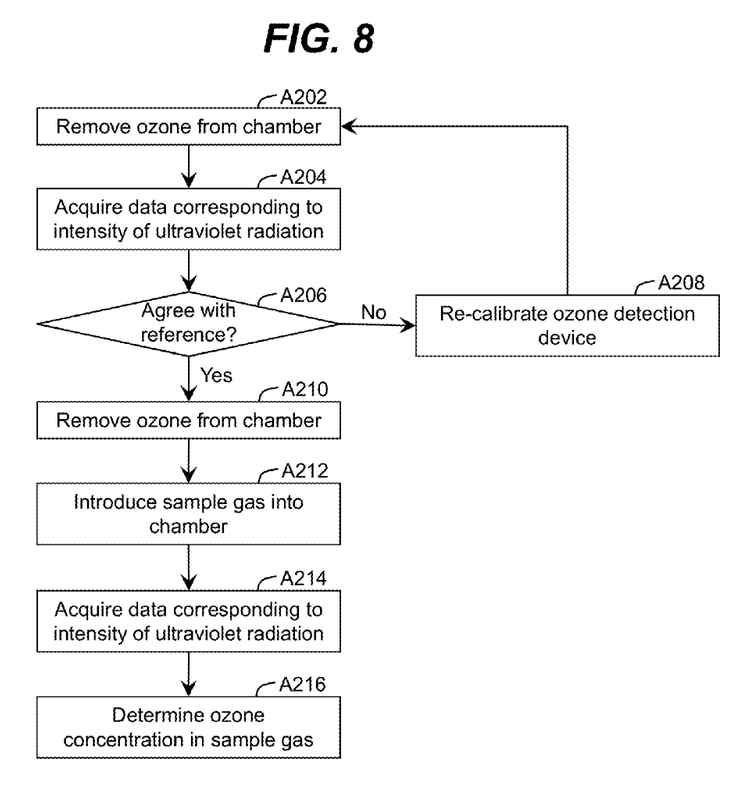
FIG. 8 shows an illustrative process for measuring an ozone concentration in a sample gas according to an embodiment.

The computer system 20 can subsequently use the calibration data to measure an ozone concentration in sample gas(es). To this extent, FIG. 8 shows an illustrative process for measuring an ozone concentration in a sample gas, which can be implemented by the computer system 20 using the ozone detection component 40A, according to an embodiment.

Initially, the computer system 20 can determine whether the calibration data remains valid. To this extent, in action A202, the computer system 20 can remove ozone from (or provide a known ozone concentration to) the chamber 42 and in action A204, the computer system 20 can acquire data corresponding to an intensity of the ultraviolet radiation detected by the ultraviolet detector 46 using any solution. For example, the computer system 20 can implement a solution similar to that described in conjunction with calibrating the ozone detection component 40A. In action A206, the computer system 20 can determine whether the intensity of the ultraviolet radiation agrees with the zero ozone level (or the known ozone concentration) reference ultraviolet intensity. If not, in action A208, the computer system 20 can re-calibrate the ozone detection component 40A using any solution. Furthermore, the computer system 20 can provide a warning for presentation to a user 12. In an embodiment, the computer system 20 can use one or more additional or alternative ozone concentrations as part of validating the calibration data.

When the computer system 20 successfully validates the calibration data, in action A210, the computer system 20 can remove ozone from the chamber 42 using any solution, e.g., by operating the filtering unit 66 to activate an ozone filter 67, operating the pumping system 64 to cause ozone-filtered sample gas to enter the chamber 42, and/or the like, as described herein. In action A212, the computer system 20 can introduce the sample gas into the chamber 42 using any solution. In an embodiment, the computer system 20 creates a partial vacuum in the chamber 42 prior to introducing the sample gas. For example, the computer system 20 can operate the pumping system 64 to cause air in the chamber 42 to be pumped out through the inlet 60 while the outlet 62 is closed.

Subsequently, the sample gas is flown into the chamber 42 (e.g., via the inlet 60 and/or the outlet 62) until the gas pressure inside the chamber 42 is approximately equal to the gas pressure outside the chamber 42. The computer system 20 can further operate the pumping system 64 to flow sample gas into the chamber 42 while the outlet 62 is open to allow gas to escape from the chamber 42. In an embodiment, the computer system 20 can operate the pumping system 64 for a sufficient amount of time to allow at least several (e.g., three) chamber volumes of gas to flow through the outlet 62.

In action A214, the computer system 20 can acquire data corresponding to an intensity of the ultraviolet radiation detected by the ultraviolet detector 46 using any solution. For example, the computer system 20 can seal the chamber 42 (e.g., by stopping the pumping system 64, closing the inlet 60, closing the outlet 62, and/or the like). The computer system 20 also can operate the ultraviolet source 44 to emit ultraviolet radiation 48, and obtain data corresponding to a detected intensity of the ultraviolet radiation 48 from the ultraviolet detector 46. The computer system 20 can store the data as detection data 34.

In action A216, the computer system 20 can determine an ozone concentration in the sample gas using the data corresponding to the detected intensity of the ultraviolet radiation 48 and the calibration data. For example, the computer system 20 can: compare the detected intensity to the reference table to deduce the ozone concentration; interpolate the data based on the reference table to find the ozone concentration; use the calibration curve to determine the ozone concentration; and/or the like.

It is understood that the process described herein for evaluating an ozone concentration in a sample gas is only illustrative of various solutions. For example, in an embodiment, the computer system 20 can determine the ozone concentration based on ultraviolet absorption using the Beer-Lambert absorption law. In this case, sufficiently accurate knowledge of a length of the optical path of the ultraviolet radiation is required, which can be available, for example, when collimated ultraviolet radiation is used as described herein.

In an embodiment, the ozone detection component 40A can include one or more additional devices, which can be utilized to obtain more accurate measurement data for the ozone concentration. To this extent, the ozone detection component 40A is shown including a temperature sensor 61 and a pressure sensor 63, each of which can provide data corresponding to the sample gas (e.g., the atmosphere surrounding the ozone detection component 40A) to the computer system 20. The computer system 20 can account for the temperature and/or pressure when generating and/or using the calibration data. For example, the computer system 20 can generate and utilize multiple sets of calibration data, each of which corresponds to a unique temperature/pressure combination. Furthermore, when the temperature/pressure of a sample gas differs from that of any of the sets of calibration data, the computer system 20 can generate another set of calibration data and/or utilize an ozone concentration derived by combining ozone concentration values obtained from multiple sets of calibration data (e.g., calibration data corresponding to the closest lower and closest higher temperatures).

While shown and described herein as a method and system for detecting a presence and/or determining a concentration of a trace gas in an atmosphere (e.g., a sample gas), it is understood that aspects of the invention further provide various alternative embodiments. For example, in one embodiment, the invention provides a computer program fixed in at least one computer-readable medium, which when executed, enables a computer system to detect the presence and/or determine the concentration of the trace gas in the atmosphere. To this extent, the computer-readable medium includes program code, such as the detection program 30 (FIG. 1), which enables a computer system to implement some or all of a process described herein. It is understood that the term "computer-readable medium" comprises one or more of any type of tangible medium of expression, now known or later developed, from which a copy of the program code can be perceived, reproduced, or otherwise communicated by a computing device. For example, the computer-readable medium can comprise: one or more portable storage articles of manufacture; one or more memory/storage components of a computing device; paper; and/or the like.

In another embodiment, the invention provides a method of providing a copy of program code, such as the detection program 30 (FIG. 1), which enables a computer system to implement some or all of a process described herein. In this case, a computer system can process a copy of the program code to generate and transmit, for reception at a second, distinct location, a set of data signals that has one or more of its characteristics set and/or changed in such a manner as to encode a copy of the program code in the set of data signals. Similarly, an embodiment of the invention provides a method of acquiring a copy of the program code, which includes a computer system receiving the set of data signals described herein, and translating the set of data signals into a copy of the computer program fixed in at least one computer-readable medium. In either case, the set of data signals can be transmitted/received using any type of communications link.

In still another embodiment, the invention provides a method of generating a system for detecting a presence and/or determining a concentration of a trace gas in an atmosphere. In this case, the generating can include configuring a computer system, such as the computer system 20 (FIG. 1), to implement the method of detecting a presence and/or determining the concentration of the trace gas in the atmosphere. The configuring can include obtaining (e.g., creating, maintaining, purchasing, modifying, using, making available, etc.) one or more hardware components, with or without one or more software modules, and setting up the components and/or modules to implement a process described herein. To this extent, the configuring can include deploying one or more components to the computer system, which can comprise one or more of: (1) installing program code on a computing device; (2) adding one or more computing and/or I/O devices to the computer system; (3) incorporating and/or modifying the computer system to enable it to perform a process described herein; and/or the like.

The foregoing description of various aspects of the invention has been presented for purposes of illustration and description. It is not intended to be exhaustive or to limit the invention to the precise form disclosed, and obviously, many modifications and variations are possible. Such modifications and variations that may be apparent to an individual in the art are included within the scope of the invention as defined by the accompanying claims.

What is claimed is:

1. A system comprising:
    a chamber having a plurality of chamber walls forming a wider central region of the chamber to lengthen an optical path of an ultraviolet beam emitted therein;
    an ultraviolet source mounted on a first interior surface of the chamber, wherein the ultraviolet source includes a set of solid state light emitting diodes;

an ultraviolet detector mounted on the first interior surface of the chamber, wherein the plurality of chamber walls of the chamber comprise reflecting walls having an ultraviolet reflection coefficient of at least eighty percent;

a set of beam guiding components optically coupled to the ultraviolet source and the ultraviolet detector, wherein the set of beam guiding components is configured to direct the ultraviolet beam onto a surface of the ultraviolet detector and further lengthen the optical path of the ultraviolet beam between the ultraviolet source and the ultraviolet detector, and wherein the set of beam guiding components includes:

a grooved plate structure, wherein the grooved plate structure includes a first groove plate and a second groove plate, wherein the first and second groove plates are in parallel and positioned in a staggered arrangement with each other, wherein the ultraviolet beam is reflected back and forth between the first groove plate and the second groove plate before being directed to the ultraviolet detector; and at least one prism configured to direct the ultraviolet beam from at least one of: the ultraviolet source or the grooved plate structure; and a computer system for evaluating a sample gas in the chamber for a presence of a trace gas by performing a method including:

operating the ultraviolet source in a high power pulse mode;

acquiring data corresponding to an intensity of ultraviolet radiation detected by the ultraviolet detector during the operating; and determining the presence of the trace gas using the acquired data.

2. The system of claim 1, further comprising:

a pumping system for introducing the sample gas into the chamber through an inlet; and an outlet, wherein the method further includes:

operating the pumping system with both the inlet and the outlet open to allow at least three chamber volumes of air to leave the chamber through the outlet; and sealing the chamber prior to operating the ultraviolet source.

3. The system of claim 2, further comprising a filter for filtering the trace gas from air prior to entering the chamber, wherein the method further includes:

operating the pumping system with the filter removing the trace gas from air entering the chamber; and operating the pumping system without the filter to introduce the sample gas into the chamber after the trace gas has been removed.

4. The system of claim 1, wherein the chamber is formed of:

a first conical frustum having a first open base and a first open top, the first open base separated from the first open top by a first height; and a second conical frustum having a second open base and a second closed top, the second open base separated from the second open top by a second height, wherein the first open top is attached to the first interior side of the chamber, and wherein the first open base is attached to the second open base, wherein each of the first and second conical frustums has an opening angle in a range between approximately twenty and approximately fifty degrees, and wherein a length of an effective optical path for an ultraviolet beam from ultraviolet light emitted by the ultraviolet source is at least a minimum target length, wherein the length of the effective optical path is a function of the opening angle and the first height of the first conical frustum, and the opening angle and the second height of the second conical frustum.

5. The system of claim 1, further comprising a parabolic reflector, wherein the ultraviolet source is located at a focal point of the parabolic reflector, and wherein the parabolic reflector forms an ultraviolet beam from ultraviolet light emitted by the ultraviolet source.

6. The system of claim 1, wherein the at least one prism and the grooved plate structure are formed of ultraviolet transparent material having an index of refraction greater than 1.42.

7. The system of claim 1, wherein the at least one prism comprises a first prism and a second prism, wherein the first prism directs the ultraviolet beam of ultraviolet light from the ultraviolet source to the first groove plate and the second groove plate, the second prism receiving the ultraviolet beam reflected back and forth between the first groove plate and the second groove plate and directing the ultraviolet beam to the ultraviolet detector.

8. The system of claim 5, wherein a ratio of a diameter of the parabolic reflector to a characteristic size of the ultraviolet source is at least five.

9. The system of claim 1, wherein each of the ultraviolet detector and the ultraviolet source comprises an ultraviolet light emitting diode configured to emit ultraviolet radiation having a peak wavelength between 240 and 290 nanometers, and wherein the computer system is configured to operate either of the ultraviolet light emitting diodes in reverse bias to function as the ultraviolet detector.

10. The system of claim 1, further comprising a trace gas source configured to produce gas having any of a plurality of known concentrations of the trace gas and to supply the gas into the chamber, wherein the computer system is further configured to generate calibration data using the gas supplied by the trace gas source for each of the plurality of known concentrations, the calibration data including measured ultraviolet intensity for each of the known ozone concentrations and an amount of ultraviolet light absorbed at each of the known ozone concentrations, and wherein the determining further uses the calibration data to ascertain the presence of the trace gas in the sample gas.

11. The system of claim 1, wherein the trace gas is ozone.

12. A system comprising:

a chamber having an inlet, an outlet and a chamber floor;

a pumping system for introducing a gas into the chamber through the inlet;

an ultraviolet source mounted on the chamber floor of the chamber;

an ultraviolet detector mounted on the chamber floor of the chamber;

a prism optically coupled to the ultraviolet source;

a grooved plate structure configured to direct an ultraviolet beam of ultraviolet light emitted from the ultraviolet source onto a surface of the ultraviolet detector, the grooved plate structure including a first groove plate and a second groove plate, the first and second groove plates being in parallel and positioned in a staggered arrangement with each other, wherein the prism directs the ultraviolet beam of ultraviolet light from the ultraviolet source to the first groove plate and the second groove plate, wherein the ultraviolet beam is reflected back and forth between the first groove plate and the second groove plate, and directed eventually to the ultraviolet detector; and a computer system for evaluating a sample gas in the chamber for a presence of ozone by performing a method including:

operating the pumping system to introduce the sample gas into the chamber, wherein the operating includes operating the pumping system with both the inlet and the outlet open for a sufficient time to allow at least three chamber volumes of gas to leave the chamber through the outlet;

sealing the chamber;

operating the ultraviolet source in a high power pulse mode after the sealing;

acquiring data corresponding to an intensity of ultraviolet radiation detected by the ultraviolet detector during the operating; and determining the presence of ozone in the sample gas using the acquired data.

13. The system of claim 12, further comprising a filter for filtering ozone from the gas prior to entering the chamber, wherein the method further includes operating the pumping system with the filter removing ozone from gas entering the chamber prior to the operating the pumping system to introduce the sample gas into the chamber.

14. The system of claim 12, wherein the determining further uses calibration data corresponding to ultraviolet radiation intensities for a plurality of known concentrations of ozone, and wherein the method further includes determining whether the calibration data remains valid prior to the operating the pumping system to introduce the sample gas, wherein the calibration data remains valid in response to determining that an intensity of ultraviolet radiation associated with each of the plurality of known concentrations of ozone agrees with a corresponding reference ultraviolet intensity.

15. The system of claim 12, wherein the method further includes operating the pumping system to form a partial vacuum in the chamber prior to the operating the pumping system to introduce the sample gas into the chamber.

16. A method of evaluating a sample gas for a presence of ozone, the method comprising:

a computer system operating a pumping system with a filter removing ozone from gas entering a chamber;

the computer system operating the pumping system without the filter removing ozone to introduce the sample gas into the chamber, wherein the operating includes operating the pumping system with both an inlet and an outlet of the chamber open for a sufficient time to allow at least three chamber volumes of gas to leave the chamber through the outlet;

the computer system sealing the chamber;

the computer system operating an ultraviolet source mounted to a first interior surface of the chamber in a high power pulse mode after the sealing, wherein the ultraviolet source includes a set of solid state light emitting diodes;

the computer system acquiring data corresponding to an intensity of ultraviolet radiation detected by an ultraviolet detector mounted to the first interior surface of the chamber during the operating, wherein the chamber includes:

a grooved plate structure optically coupled to the ultraviolet source and the ultraviolet detector and configured to lengthen an optical path of an ultraviolet beam between the ultraviolet source and the ultraviolet detector, wherein the grooved plate structure includes a first groove plate and a second groove plate, wherein the first and second groove plates are in parallel and positioned in a staggered arrangement with each other, wherein the ultraviolet beam is reflected back and forth between the first groove plate and the second groove plate before being directed to the ultraviolet detector; and at least one prism configured to direct the ultraviolet beam from at least one of: the ultraviolet source or the grooved plate structure; and the computer system determining the presence of ozone in the sample gas using the acquired data.

17. The method of claim 16, wherein the determining further uses calibration data corresponding to ultraviolet radiation intensities for a plurality of known concentrations of ozone, and wherein the method further includes the computer system determining whether the calibration data remains valid prior to the operating the pumping system to introduce the sample gas, wherein the calibration data remains valid in response to determining that an intensity of ultraviolet radiation associated with each of the plurality of known concentrations of ozone agrees with a corresponding reference ultraviolet intensity.

18. The method of claim 17, wherein the method further includes generating new calibration data in response to determining that the calibration data is no longer valid.

19. The method of claim 16, wherein the method further includes the computer system operating the pumping system to form a partial vacuum in the chamber prior to the operating the pumping system to introduce the sample gas into the chamber.

20. The system of claim 1, wherein the first interior surface of the chamber is a floor of the chamber, and wherein at least one of the plurality of chamber walls is parabolic.

* * * * *